US00PP25555P2

(12) United States Plant Patent
Pieters et al.

(10) Patent No.: US PP25,555 P2
(45) Date of Patent: May 12, 2015

(54) ***GUZMANIA* PLANT NAMED 'AMORETTO'**

(50) Latin Name: *Guzmania hybrida*
Varietal Denomination: Amoretto

(71) Applicants: Luc Pieters, Laarne (BE); Caroline De Meyer, Laarne (BE)

(72) Inventors: Luc Pieters, Laarne (BE); Caroline De Meyer, Laarne (BE)

( * ) Notice: Subject to any disclaimer, the term of this patent is extended or adjusted under 35 U.S.C. 154(b) by 108 days.

(21) Appl. No.: 13/815,656

(22) Filed: Mar. 13, 2013

(51) Int. Cl.
*A01H 5/00* (2006.01)

(52) U.S. Cl.
USPC ..... Plt./371

(58) Field of Classification Search
USPC ..... Plt./371
See application file for complete search history.

*Primary Examiner* — Annette Para
(74) *Attorney, Agent, or Firm* — C. A. Whealy

(57) ABSTRACT

A new and distinct cultivar of *Guzmania* plant named 'Amoretto', characterized by its compact, upright and outwardly arching growth habit; dark green-colored leaves; inflorescences held upright and above foliage on strong scapes; inflorescences with showy orange red-colored bracts; and good postproduction longevity.

2 Drawing Sheets

Botanical designation: *Guzmania hybrida.*
Cultivar denomination: 'AMORETTO'.

BACKGROUND OF THE INVENTION

The present invention relates to a new and distinct cultivar of *Guzmania* plant, botanically known as *Guzmania hybrida* and hereinafter referred to by the name 'Amoretto'.

The new *Guzmania* plant is a product of a planned breeding program conducted by the Inventors in Laarne, Belgium. The objective of the breeding program is to create new *Guzmania* plants having unique flower colors and enhanced postproduction longevity.

The new *Guzmania* originated from a cross-pollination made by the Inventors in May, 2007 in Laarne, Belgium of an unnamed proprietary selection of *Guzmania hybrida*, not patented, as the female, or seed, parent with unnamed proprietary selection of *Guzmania wittmackii,* not patented, as the male, or pollen, parent. The new *Guzmania* plant was discovered and selected by the Inventor as a single flowering plant from within the progeny of the stated cross-pollination in a controlled environment in Laarne, Belgium in November, 2007.

Asexual reproduction of the new *Guzmania* plant by tissue culture in a controlled environment in Laarne, Belgium since December, 2007 has shown that the unique features of this new *Guzmania* plant are stable and reproduced true to type in successive generations.

SUMMARY OF THE INVENTION

Plants of the new *Guzmania* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Amoretto'. These characteristics in combination distinguish 'Amoretto' as a new and distinct *Guzmania* plant:

1. Compact, upright and outwardly arching growth habit.
2. Dark green-colored leaves.
3. Inflorescences held upright and above foliage on strong scapes.
4. Inflorescences with showy orange red-colored bracts.
5. Good postproduction longevity.

Plants of the new *Guzmania* can be compared to plants of the female parent selection. Plants of the new *Guzmania* differ primarily from plants of the female parent selection in plant size as plants of the new *Guzmania* are larger than plants of the female parent selection.

Plants of the new *Guzmania* can be compared to plants of the male parent selection. Plants of the new *Guzmania* differ primarily from plants of the male parent selection in inflorescence bract color as plants of the new *Guzmania* have orange red-colored bracts whereas plants of the male parent selection have orange-colored bracts.

Plants of the new *Guzmania* can be compared to plants of *Guzmania hybrida* 'Ostara', not patented. In side-by-side comparisons conducted in Laarne, Belgium, plants of the new *Guzmania* and 'Ostara' differed in the following characteristics:

1. Plants of the new *Guzmania* had shorter and broader leaves than plants of 'Ostara'.
2. Plants of the new *Guzmania* flowered for a longer period of time than plants of 'Ostara'.
3. Plants of the new *Guzmania* and 'Ostara' differed in inflorescence bract color as plants of 'Ostara' had lighter-colored bracts.

BRIEF DESCRIPTION OF THE PHOTOGRAPHS

The accompanying colored photographs illustrate the overall appearance of the new *Guzmania* plant showing the colors as true as it is reasonably possible to obtain in colored reproductions of this type. Colors in the photographs may differ slightly from the color values cited in the detailed botanical description which accurately describe the colors of the new *Guzmania* plant.

The photograph on the first sheet comprises a side perspective view of a typical flowering plant of 'Amoretto' grown in a container.

The photograph on the second sheet is a close-up view of a typical inflorescence of 'Amoretto'.

DETAILED BOTANICAL DESCRIPTION

The aforementioned photographs and following observations, measurements and values describe plants grown during the winter in 13-cm containers in a glass-covered greenhouse in Laarne, Belgium and under cultural practices typical of commercial *Guzmania* production. During the production of the plants, day temperatures ranged from 21° C. to 30° C., night temperatures ranged from 20° C. to 21° C. and maximum light levels were about 18,000 lux. Plants were three years old when the photographs and description were taken. In the following description, color references are made to The Royal Horticultural Society Colour Chart, 2007 Edition, except where general terms of ordinary dictionary significance are used.

Botanical classification: *Guzmania hybrida* 'Amoretto'.

Parentage:

*Female, or seed, parent*.—Unnamed proprietary selection of *Guzmania hybrida*, not patented.

*Male, or pollen, parent*.—Unnamed proprietary selection of *Guzmania wittmackii*, not patented.

Propagation:

*Type*.—By tissue culture.

*Root description*.—Thick, fleshy; creamy white in color.

*Rooting habit*.—Medium density.

Plant description:

*Plant and growth habit*.—Compact, upright and outwardly arching plant habit; basal rosette of outwardly curved strap-like leaves affixed in tight spiral ranks; terminal inflorescence on an upright scape which emerges from the center of the basal rosette; moderately vigorous growth habit.

*Plant height, soil surface to top of inflorescence*.—About 54.5 cm.

*Plant diameter or spread*.—About 67.5 cm.

Foliage description:

*Arrangement*.—Basal rosette, spiral phyllotaxis; leaves sessile.

*Quantity of leaves per plant*.—Plants typically produce about 25 leaves prior to inflorescence development.

*Shape*.—Ligulate.

*Apex*.—Apiculate.

*Margin*.—Entire.

*Length*.—About 38.8 cm.

*Width*.—About 4.8 cm.

*Aspect*.—Leaves curved outward over their length and arching downward towards the apex.

*Texture, upper and lower surfaces*.—Leathery, stiff; smooth, glabrous.

*Venation*.—Parallel.

*Color*.—Developing leaves, upper surface: Close to N137A; towards the base, close to 146D. Developing leaves, lower surface: Close to 146A; towards the base, close to 146D. Fully expanded leaves, upper surface: Close to between N137A and 147A; towards the base, close to 146C to 146D; venation, similar to lamina colors. Fully expanded leaves, lower surface: Close to between 146A and 147B; towards the base, close to 146C to 146D; venation, similar to lamina colors.

Inflorescence description:

*Inflorescence form*.—Terminal inflorescences with showy bracts; inflorescences supported on erect and strong scapes.

*Inflorescence length*.—About 16 cm.

*Inflorescence width*.—About 23 cm.

*Fragrance*.—None detected.

*Inflorescence longevity*.—Inflorescences of the new *Guzmania* are long-lasting; bract coloration is maintained for about four to five months; inflorescences persistent.

*Natural flowering season*.—Plants of the new *Guzmania* typically flower during the winter.

*Flowers*.—Arrangement: Single small flowers in clusters with about 120 flowers developing per inflorescence; flowers are clustered near the apex of the inflorescence and open more or less simultaneously. Diameter: About 4 mm. Depth (height): About 4.9 cm.

*Flower buds*.—Length: About 3.6 cm. Diameter: About 4 mm. Shape: Lanceolate. Color: Close to 14A to 14B.

*Petals*.—Quantity per flower and arrangement: Six petals arranged in two whorls. Length: About 1.9 cm. Width: About 4 mm. Shape: Lanceolate. Apex: Acute. Color, immature and mature: Close to 13A; towards the apex, close to 17A to 17B; towards the base, close to 150C.

*Sepals*.—Quantity per flower: One. Length: About 4.9 cm. Width: About 4 mm. Shape: Lanceolate. Apex: Broadly acute to obtuse. Base: Broadly cuneate. Color, immature and mature: Close to 8B; towards the apex, close to 9B.

*Scape*.—Length: About 42 cm. Diameter: About 1 cm. Strength: Strong. Aspect: Typically erect. Texture: Smooth, glabrous. Color: Close to 145A.

*Reproductive organs*.—Stamens: Quantity per flower: Six. Filament length: About 9 mm. Anther length: About 7 mm. Anther shape: Lanceolate. Anther color: Close to 155A. Pollen: None observed. Pistils: Quantity per flower: One. Pistil length: About 1 cm. Style length: About 8 mm. Style color: Close to 154D. Stigma shape: Clavate, three-lobed. Stigma color: Close to 154C to 154D. Ovary color: Close to 154C.

*Seeds and fruits*.—Seed and fruit production has not been observed on plants of the new *Guzmania*.

*Terminal bracts*.—Length: About 15.1 cm. Width: About 3.9 cm. Shape: Lanceolate or ligulate. Apex: Acute. Base: Sheathing the scape. Margins: Entire. Texture, upper and lower surfaces: Smooth, glabrous. Color, upper surface: Close to N30A becoming closer to 33A; towards the base, close to 145C. Color, lower surface: Close to 34A; towards the base, close to N144A.

*Scape bracts*.—Length: About 19.2 cm. Width: About 3.8 cm. Shape: Lanceolate or ligulate. Apex: Acute. Base: Sheathing the scape. Margins: Entire. Texture, upper and lower surfaces: Smooth, glabrous. Color, upper surface: Close to 34A; towards the apex, close to N137B. Color, lower surface: Close to 42A; towards the apex, close to 146A to 146B.

Temperature tolerance: Plants of the new *Guzmania* have been observed to tolerate high temperatures about 40° C. and to be hardy to USDA Hardiness Zone 10.

Disease & pest resistance: Plants of the new *Guzmania* have not been observed to resistant to pathogens and pests common to *Guzmania* plants.

It is claimed:

1. A new and distinct *Guzmania* plant named 'Amoretto' as illustrated and described.

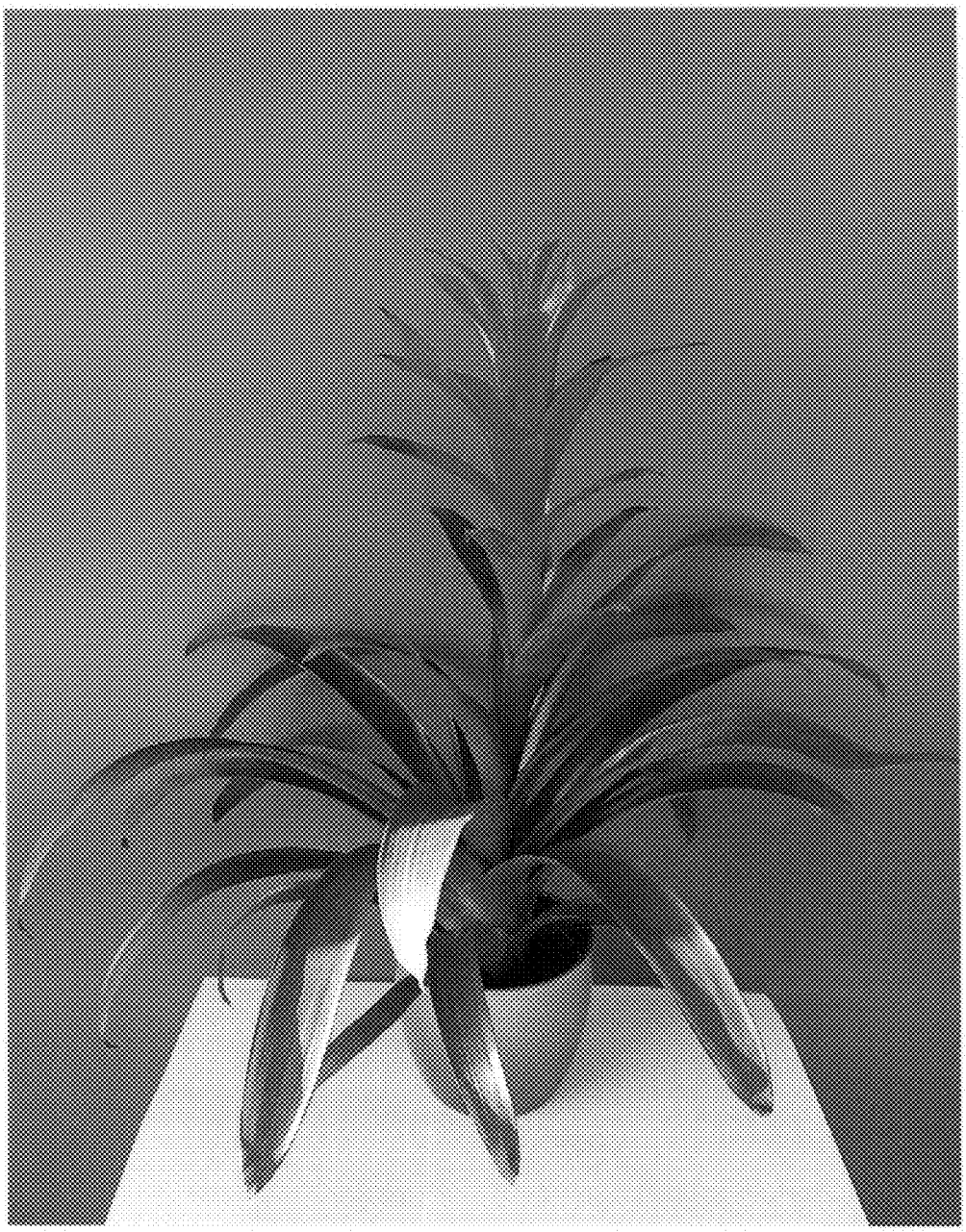

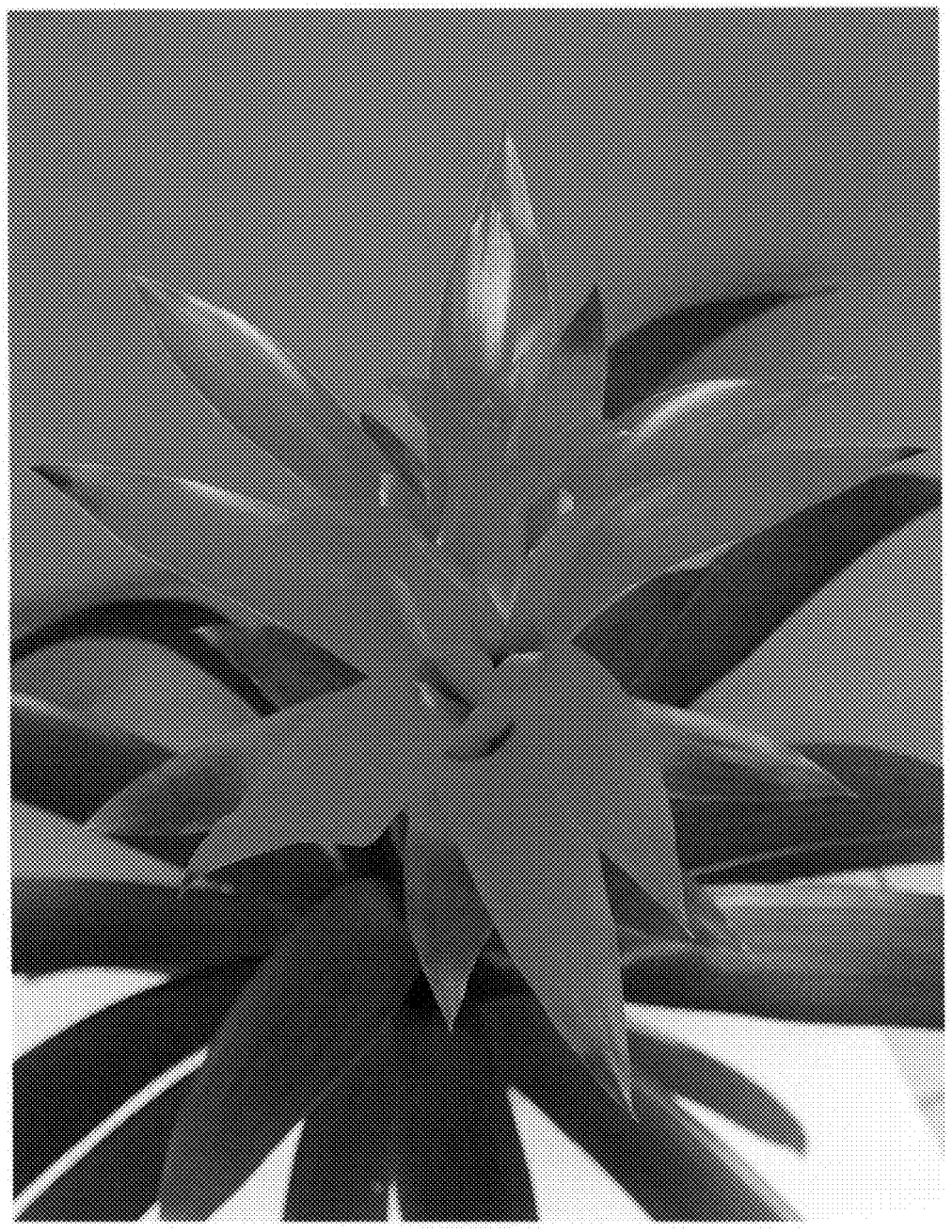

* * * * *